United States Patent [19]

Schumacher

[11] Patent Number: 4,917,238

[45] Date of Patent: Apr. 17, 1990

[54] WASTE CLEANUP KIT

[76] Inventor: Donovan J. Schumacher, 421 13th Ave. West, Williston, N. Dak. 58801

[21] Appl. No.: 342,596

[22] Filed: Apr. 21, 1989

Related U.S. Application Data

[63] Continuation of Ser. No. 198,569, May 25, 1988, abandoned.

[51] Int. Cl.[4] .............................................. B65D 69/00
[52] U.S. Cl. .................................... 206/223; 206/570; 206/572; 206/568
[58] Field of Search ............... 206/223, 278, 440, 569, 206/570, 572, 568; 119/1; 294/1.3, 55

[56] References Cited

U.S. PATENT DOCUMENTS

| | | | |
|---|---|---|---|
| 1,974,838 | 9/1934 | Schmid . | |
| 2,799,563 | 7/1957 | Shenker . | |
| 3,041,778 | 7/1962 | Seron . | |
| 3,108,803 | 10/1963 | Naideth . | |
| 3,154,052 | 10/1964 | Sweeney | 119/1 |
| 3,286,826 | 11/1966 | Stoll . | |
| 3,355,837 | 12/1967 | Pedersen . | |
| 3,572,997 | 3/1971 | Burk . | |
| 4,018,332 | 4/1977 | Benda . | |
| 4,186,955 | 2/1980 | Campbell | 294/1.3 |
| 4,205,869 | 6/1980 | Mathis . | |
| 4,294,349 | 10/1981 | Ibsen et al. . | |
| 4,357,961 | 11/1982 | Chick . | |
| 4,364,473 | 12/1982 | Bogaert . | |
| 4,437,568 | 3/1984 | Hamblin | 206/570 |
| 4,595,102 | 6/1986 | Cianci et al. . | |
| 4,715,495 | 12/1987 | Henry . | |
| 4,779,567 | 10/1988 | Smith | 119/1 |

Primary Examiner—David T. Fidei
Attorney, Agent, or Firm—Timothy R. Conrad

[57] ABSTRACT

A waste cleanup kit is disclosed comprising a box and a plurality of kit contents. The contents include an absorbent material, a disinfectant and a scoop for scooping up waste material and a scraper for scraping waste material from a surface. The contents further include at least one glove for use by an operator and an absorbent towel. The contents further include a germicidal handwipe and a plastic bag sized to contain a scoop together with waste material. The absorbent material and the disinfectant are disposed in a separate material container and a disinfectant container, respectively. Each of the absorbent material container, disinfectant container, scoop, scraper, glove, towel, wipe and bag are disposed within the box.

8 Claims, 1 Drawing Sheet

U.S. Patent
Apr. 17, 1990
4,917,238
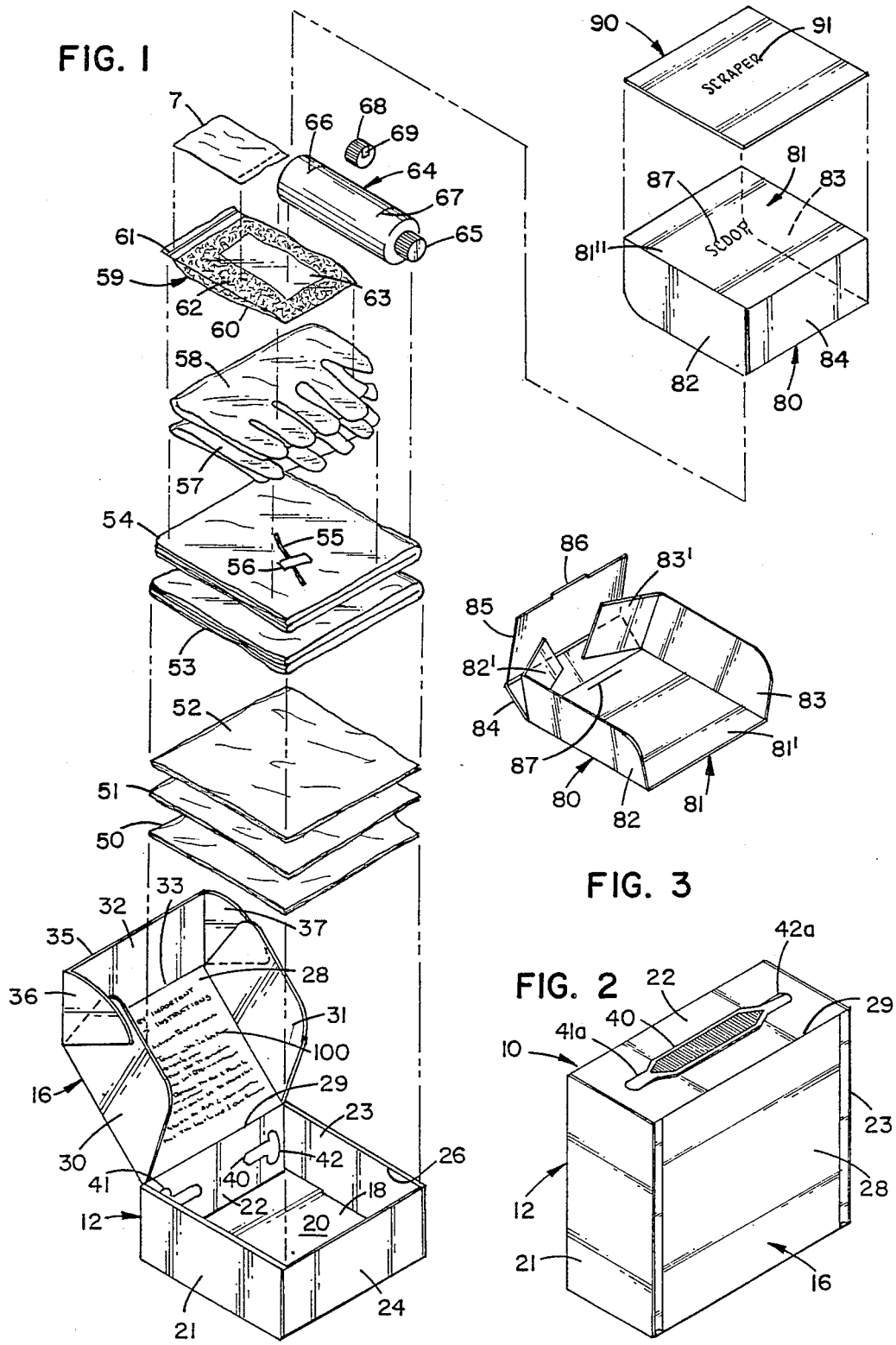

WASTE CLEANUP KIT

This is a continuation of application Ser. No. 198,569, filed May 25, 1988.

BACKGROUND OF THE INVENTION

1. Field of the Invention

This application pertains to a cleanup kit. More particularly, this application pertains to a kit for cleaning up body substances while abating infection from diseases carried by the substances.

2. Description of the Prior Art

Disposal of waste products has long been addressed in the prior art. For example, each of U.S. Pat. Nos. 4,715,495; 4,205,869 and 3,286,826 all teach kits for disposing of animal waste.

In recent years, the need for disposal of waste carries with it a concurrent concern for avoidance of transfer of communicable diseases. Risk of disease transfer is particularly acute where the waste to be disposed is human vomit, blood, feces or urine. In such instances, the risk of Hepatitis B or AIDS virus transfer must be addressed.

The need for cleanup kits for disposing of human waste while dressing infection control concerns is particularly acute in certain environments. For example, in public facilities such as schools and restaurants, public transportation such airplanes and buses as well as day-care centers and other environments, the need to dispose of human waste (particularly vomit) frequently arises. It is an object of the present invention to provide a kit for cleaning up human waste in a manner which abates risk of transfer of infectious diseases to the person cleaning the waste. Another object of the present invention is to provide such a cleanup kit which may be used for a single instance of waste cleanup and readily disposed.

SUMMARY OF THE INVENTION

According to the preferred embodiment of the present invention, a waste cleanup kit is disclosed which includes a box having a plurality of kit contents. The kit contents include an absorbent material, a disinfectant and a scoop for scooping up waste material. A scraper is provided for scraping waste material from a surface. At least one glove for use by an operator and one absorbent towel is provided as part of the kit contents. Further, the kit includes at least one germicidal handwipe. A plastic bag is provided with and sized to contain at least said scoop, glove and towel with means for closing the bag after use. The absorbent material and the disinfectant are disposed in separate containers with each of the containers, scoop, scraper, glove, towel, wipe and bag dispose within the box.

BRIEF DESCRIPTION OF THE DRAWINGS

FIG. 1 is a perspective view in exploded format showing a kit of the present invention with its separate elements removed from the kit;

FIG. 2 is a perspective view of the cleanup kit with a box of the kit shown in a closed position.

FIG. 3 is a perspective view of a scoop for use with the present invention with a scoop shown in a partially collapsed state.

DESCRIPTION OF THE PREFERRED EMBODIMENT

With reference down to the various figures in which identical elements are numbered identically throughout, the kit for cleaning up body waste such as vomit, blood, feces and the like is shown generally at 10. The kit includes a box 12 formed from a sheet of corregated cardboard. Box 12 includes a bottom wall 18 and four posing sidewalls 21-24. Sidewalls 21-24 and bottom wall 18 cooperate to define a box interior 20 having a generally rectangular opening 26.

A lid 16 includes a cover plate 28 sized to cover opening 26 with cover plate hinged to sidewall 22 at a hinge line 29. Preferably, lid 26 and sidewall 22 form part of a continuous sheet of corregated cardboard.

Extending from opposing side edges of cover plate 28 are opposing side flaps 30 and 31. Side flaps 30 and 31 are dimensioned to be received abutting sidewalls 21, 23, respectively with sidewalls 30 and 31 dimensioned to retain cover plate 28 in spaced relation from bottom plate 18 with cover plate 28 approximately coplanar with opening 26.

An end flap 32 is hingedly connected to cover plate 28 at a hinge line 33 and is likewise dimensioned such that the length from hinge line 33 to an end 35 of flap 32 is approximately equal to the desired depth of box interior 20. Overlapping flaps 36 and 37 extending from flap 32 cover side flaps 30 and 31 such that lid 16 can be folded by an operator into a boxlike configuration with flaps 30, 36 and flaps 31, 37 in generally planer alignment and abutting sidewalls 21 and 23, respectively and with flap 32 abutting in face-to-face alignment with sidewall 24 to thereby define an enclosed box as shown in FIG. 2.

A handle 40 is provided connected to sidewall 22 with handle 40 provided in the form of a strap having tabbed ends 41 and 42 extending through slots 41a, 42a in sidewall 22. An operator grasps handle 40 with handle 40 flexing away from sidewall 21. The flexing accommodated by movement of ends 41 and 42 within slots 41a, 42a formed in sidewall 22.

The kit 10 includes a plurality of kit contents shown in FIG. 1. The kit contents include preferably three disposable towels 50, 51, 52 (preferably absorbent paper towels or the like). The contents further include preferably two plastic bags 53 and 54. Each of the bags is provided with closure means. The closure means for bag 54 is shown as a twist tie 55 secured to bag 53 through any suitable means such as a strip of releasable tape 56. The contents further include a pair of disposable plastics gloves 57, 58.

The contents of the package also include a package 59 of absorbent material 62. The package 59 of absorbent material includes a clear flexible pouch 60 having a press locked end 61. The contents of the pouch 60 is a metered amount of an absorbent granular material. A preferred absorbent material is commercially available mixture of clay, sawdust and deodorant. An example is Omit by Alliance Group, Milwaukee, Wis. The amount of absorbent material is selected for an anticipated one time cleanup chore. Preferably, such amount will be 4–5 ounces. The package 60 further includes a label 63 instructing the user on usage of the absorbent material as well as safety features associated with safe use of the material and first aid procedures regarding use of the material.

The contents further include a container in the form of a plastic bottle 64 and cap 65 for containing a metered amount of chlorine solution. The bottle 64 includes a first fill line 66 and a second fill line 67. Preferably, the bottle 64 is prepackaged with a concentrated (5¼%) sodium hypochlorite which is filled to fill line 66. Fill line 66 is selected so that ¾ fluid ounce of concentrate is in bottle 64. The amount of chlorine concentrate is selected such that a user can fill the remainder of the volume to fill line 67 with water to dilute the sodium hypochlorite concentrate to a desired state. The sodium hypochlorite is such that the amount of container 64 is selected for an anticipated amount needed for a one time disinfection of an area contaminated by human waste. The second file line 67 is selected so that the diluted solution comprises 6 to 7 fluid ounces. This results in a 1-to-10 chlorine solution. Left set on an infected area for about ten minutes, this concentration is effective in killing the Hepatitus B virus.

For convenience of an operator, a second cap 68 is provided having a pour spout 69 so that an operator can squeeze bottle 64 and direct a stream of disinfectant through spout 69 to a desired area. Alternatively, a user can simply remove cap 65 and pour the disinfectant in a desired area.

A germicidal handwipe 7 is provided. Handwipe 70 is preferably a chlorhexidine towelette (such as HIVI-STAT ® germicidal handwipe available through Stuart Pharmaceuticals, Wilmington, Del.) which is a pocket size disposable towelette containing chlorhexidine gluconate. The towelette is contained within a conventional foil wrapper.

Finally, the contents of the kit 10 include a scoop 80 and a scraper 90. Scoop 80 is shown in a partially collapsed state in FIG. 3.

Scoop 80 includes a base plate 81 and opposing sidewalls 82 and 83, backwall 84 with a foldover flap 85. Sidewalls 82 and 83 both include side flaps 82' and 83'. Foldover flap 85 includes a tab 86 sized to be received within a slot 87 formed in bottom wall 81. The scoop is assembled by folding sidewalls 82 and 83 to a position perpendicular to bottom plate 81 and likewise folding plate 84 to a position perpendicular to plate 81. In this position, flaps 82, and 83' are opposing and abutting backwall 84. Flap 85 is folded over flaps 82' and 83' with tab 86 received within slot 87. So formed, scoop 80 forms a completed scoop with a generally rectangular configuration with bottom plate 81 dimensioned to be approximate to the surface area of opening 26 of box 10.

Sidewalls 82 and 83 and backwall 84 are dimensioned to be approximate to the dimension of box sidewalls 21–24. Accordingly, scoop 80 may be inserted within box interior 20 with the edges of walls 82, 83, 85 abutting bottom plate 18 and with the walls 82, 83 and 85 supporting bottom plate 81 in spaced relation from plate 18 with bottom plate 81 generally coincident with opening 26. In this configuration a waste receiving surface 81' of scoop 80 opposes box bottom plate 18. Box bottom plate 18, sidewalls 82, 83 and 85 and bottom wall 81 cooperate to define a content receiving chamber sized to receive contents 50–59, 64 and 70.

For user convenience, an identifying title 87 is disposed on a bottom surface 81" of bottom plate 81 such that the label 87 is exposed to an operator who has opened lid 16 of box 10 and removed scraper 90. A scraper 90 is a flat sheet of corregated cardboard sized to cover bottom plate 81. The scraper 90 includes an identifying label 91 which is exposed to an operator who has opened lid 16. In a preferred embodiment, scraper 90 and scoop 80 are coated through commercially available means to be provided with non-stick surfaces. A preferred commercially available coating is a Michaelson coating available through North Star Container, Minneapolis, Minn.

Having described the structure of the kit of the present invention, its use will now be demonstrated. The present invention is principally intended for use with disposal of human waste. The most significant anticipated use is for disposal of human vomit which may contain viruses for infectious disease such as Hepititis B or AIDS. When cleaning and disinfecting an area of human waste such a vomit, an operator opens box 10 by opening lid 16. Upon opening lid 16, the operator is immediately presented with a detailed list of instructions 100 set forth upon an interior of lid cover plate 28.

The instructions set forth a preferred use of the present invention. This preferred method of use is for an operator to open absorbent containing pouch 60 and sprinkle or otherwise spread absorbent granular material 62 over the waste. The operator is then instructed to fill bottle 64 with water to fill line 67.

Next, using disposable gloves 57 and 58, the operator grasps scoop 80 and scraper 91 in opposing hands and scrapes the absorbent and waste material into scoop 80. The operator is next instructed to place the scoop, its contents, the scraper and the used pouch 60 in one of bags 53 and 54 and close the bag with a twist tie 55. The operator is instructed to retain the disposable gloves for further use.

The operator is next instructed to pour the diluted chlorine solution from bottle 64 over the spill area and permit it to set for a period of time (preferably 10 minutes). The operator is next instructed to use disposable towels 50 through 52 to wipe up the diluted chlorine solution from the spill area and then to place all items including the disposable gloves in the second bag 54. The operator is next instructed to use the germicidal handwipe 70 to clean the operator's hands and to discard the handwipe into the second plastic bag 54. The operator then ties the plastic bag 54 with a tie and then disposes of the bag and washes hands with soap and water.

The elements of the kit are important for the prevention of disease transmission. For example, the granular absorbent 62 deodorizes and covers the waste. The absorbent is necessary to remove organic matter before a chlorine solution disinfectant can be used and be considered effective. The gloves 57, 58 protect the operator from body substances that contain viruses or other microorganisms. The chlorine solution of bottle 64 is necessary for effective disinfecting of Hepititis B virus. It is also necessary for being effective against gram positive and gram negative bacteria and other viruses. The scraper and scoop are necessary for preliminary cleanup. Notably, gross contamination must be removed before disinfection by the chlorine solution can be effective. Therefore, the operator is instructed to remove the waste and absorbent prior to use of the chlorine solution. The germicidal hand wipe provides rapid bactericidal action and has a persistent antimicrobial effect against a wide range of microorganisms.

From the forgoing detailed description of the present invention, it has been shown how the objects of the invention have been attained in a preferred manner. However, modifications and equivalents of the disclosed concepts such as readily occur to those skilled in the art are intended to be included in the scope of this invention. Thus, the scope of the invention is intended to be limited only by the scope of the claims as are, or may hereafter be, appended hereto.

What is claimed is:

1. A waste cleanup kit comprising a main container and a plurality of kit contents including:
   an absorbent material;
   a disinfectant;
   means for scooping up waste material;
   at least one glove for use by an operator using the cleanup kit;
   at least one absorbent towel;
   at least one germicidal handwipe;
   at least one plastic bag sized to contain at least said means for scooping and means for closing said bag;
   said absorbent material and said disinfectant disposed in a separate absorbent material container and a separate disinfectant container, respectively;
   each of said absorbent material container, disinfectant container, means for scooping, glove, towel, handwipe and bag disposed within said main container.

2. A waste cleanup kit according to claim I wherein said main container comprises a box including a lid for exposing an interior of said box, said means for scooping comprising a scoop including a base and a plurality of walls sized to conform with the interior surfaces of said box with said scoop disposed within said box and with said walls supporting said base in spaced relation from a bottom of said box to define a packaging chamber sized to receive at least a plurality of said kit contents.

3. A waste cleanup kit according to claim 2 wherein said scoop is provided with a nonstick surface.

4. A waste clean-up kit according to claim 1 wherein said kit contents further include a scraper for scraping waste material from a surface.

5. A waste cleanup kit according to claim 4 wherein said scraper is provided with a nonstick surface.

6. A waste cleanup kit according to claim 1 wherein said disinfectant container includes a bottle having a first fill line and a second fill line and containing a concentrate of disinfectant filled to said first fill line with said concentrate diluted to a predetermined desired dilution upon filling said bottle with water to said second fill line.

7. A waste cleanup kit comprising a box and a plurality of kit contents including disinfectants with said box including a lid for exposing an interior of said box, said plurality of kit contents including a scoop having a base and a plurality of walls sized to conform with interior surfaces of said box with said scoop disposed within said box and with said walls supporting said base in space relation from a bottom of said box to define a packaging chamber sized to receive at least a plurality of said kit contents.

8. A waste cleanup kit according to claim 7 wherein said kit contents further include a disposable glove for use by an operator and a disposable towel, an absorbent material and at least one plastic bag sized to contain waste material collected by said scoop.

* * * * *